(12) United States Patent
Ravo

(10) Patent No.: US 6,680,421 B1
(45) Date of Patent: Jan. 20, 2004

(54) PROTECTIVE INGUINAL PERINEAL ELEMENT

(75) Inventor: Biagio Ravo, Rome American Hospital Via Emilio Longoni, 69-Rome (IT)

(73) Assignee: Biagio Ravo, Rome (IT)

( * ) Notice: Subject to any disclaimer, the term of this patent is extended or adjusted under 35 U.S.C. 154(b) by 0 days.

(21) Appl. No.: 09/553,258

(22) Filed: Apr. 20, 2000

(51) Int. Cl.[7] ................................. A61F 13/15

(52) U.S. Cl. ............................................. 604/358

(58) Field of Search ................ 604/385.01, 385.23, 604/385.17, 385.201, 304, 307, 385.04; 602/48, 67

(56) References Cited

U.S. PATENT DOCUMENTS

| | | | | |
|---|---|---|---|---|
| 2,624,336 | A | * | 1/1953 | Hansley |
| 4,605,404 | A | * | 8/1986 | Sneider |
| 4,804,380 | A | * | 2/1989 | Lassen et al. |
| 5,514,104 | A | * | 5/1996 | Cole et al. |
| 5,538,500 | A | * | 7/1996 | Peterson |
| 5,843,018 | A | * | 12/1998 | Shesol et al. |
| 6,316,688 | B1 | * | 11/2001 | Hammons et al. |

* cited by examiner

*Primary Examiner*—Dennis Ruhl
(74) *Attorney, Agent, or Firm*—Blynn L. Shideler; Krisanne Shideler; BLK Law Group

(57) ABSTRACT

A protective inguinal perineal element for male and female patients includes a cushion that, when necessary, can have a topical substance applied to it which can be released to the patient.

17 Claims, 7 Drawing Sheets

PROTECTIVE INGUINAL PERINEAL ELEMENT

BACKGROUND OF THE INVENTION

1. Field of the Invention

We, Biagio Ravo and Alberto Caramelli, have developed a thin soft flexible protective element for the perineal area of male and female patients with a cushion that, when necessary, can receive a topical substance and release the substance in the perineal area.

2. Background of the Invention

In both male and female patients, the perineal area is a critical area due to the openings that appear and for its conformation which is restricted by closed lateral walls not exposed to air. Under normal conditions, and especially in pathological conditions, the perineal area can be a place of abundant exudation, secretion and transpiration. These conditions are especially apparent when the area is affected by a small pathology such as dermatitis, inflammation, and in severe situations, wounds, infections, ulcers and the like.

In the above-mentioned conditions, it is necessary to maintain dryness and cleanliness of the area and, at times, the application of topical substances is necessary. Therefore, it can be necessary to apply an element of protection and absorption which is able to easily conform to the anatomy in question and to be stable in its location.

The object of the present invention is to provide an element of protection which addresses these conditions. The element of protection which is the object of the present application, is useful for geriatric patients who are affected by local irritations and/or pathologies. The element of protection of the present invention can be particularly useful as a hygiene barrier and protective element for geriatric, adult and pediatric patients, whether they are physically well or are affected by some local affliction.

SUMMARY OF THE INVENTION

The above objects are achieved with a protective inguinal perineal element for male and female patients with a cushion that, when necessary, can have a topical substance applied to it which can be released to the perineal area of the patient.

The present invention is a soft flexible protective element, for male and female patients for the inguinal and perineal areas, which absorbs any liquid from transpiration, exudation, secretions or the like present in these areas under normal conditions or in patients with minor or severe afflictions in these areas. The element is made of a main body of a strip form with two lateral wings. The element includes a rectangular flat central cushion attached to the main body which can be folded onto itself in a U shape and compressed at the moment it is applied to the patient.

Considering the differences in the anatomy of male and female patients, the element of the present invention, in addition to having characteristics which are common to carry out its function, should also have diversified forms that would enable application to both male and female patients. This is described in the following description and illustrated in the attached figures. The characteristics that are common for use with both male and female patients are related to the posterior portion of the element, the nature of the material in which it is made, and the conformation of the absorbent material which has a cushion or pad that, when folded onto itself, provides a tight U-shaped configuration. This cushion and the U-shaped configuration, in addition to being anatomically correct, allows for ease of placement of any substance which needs to be topically applied. This substance can be gradually released from the cushion to the patient for the time interval in which the element is applied to the patient (i.e., until the element is replaced).

These and other advantages of the present invention will be clarified in the brief description of the preferred embodiments taken together with the attached drawings wherein like reference numerals represent like elements throughout.

DETAILED DESCRIPTION OF THE PREFERRED EMBODIMENTS

Figure 1:
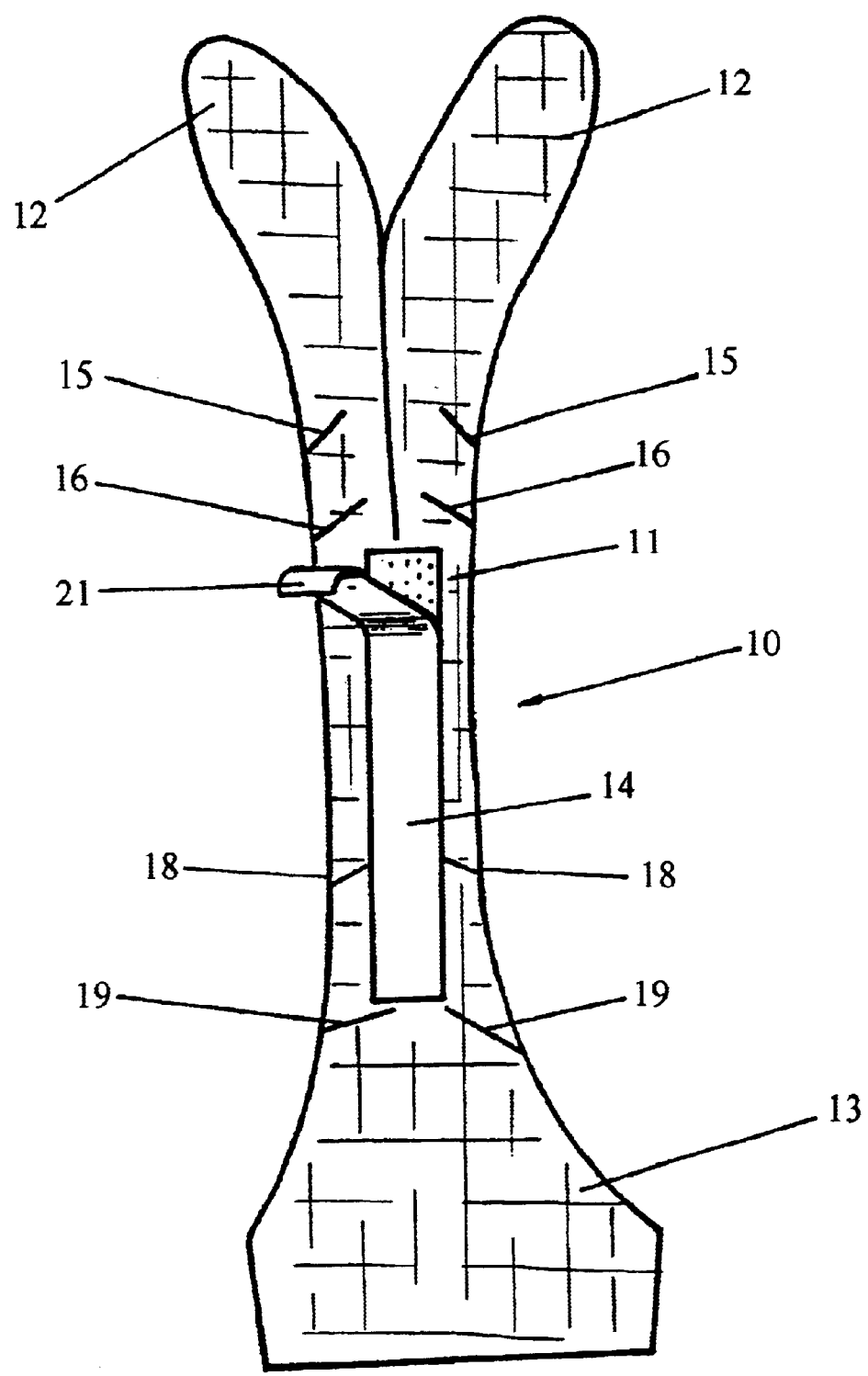
FIG. 1 is a plan view of a protective element according to one embodiment of the present invention which is designed for a male patient.

In FIGS. 1–4, the protective element 10 of the present invention is designed for a male patient and, as shown, is composed of a flat body which has a central part 11 with lateral wings 11A, 11B, two V-forming flaps 12 which can be widened out, and a posterior trapezoidal section 13. A rectangular, thicker spongy strip 14 is applied to the central part 11. The strip 14 may also be considered a cushion or a pad.

Figure 3:
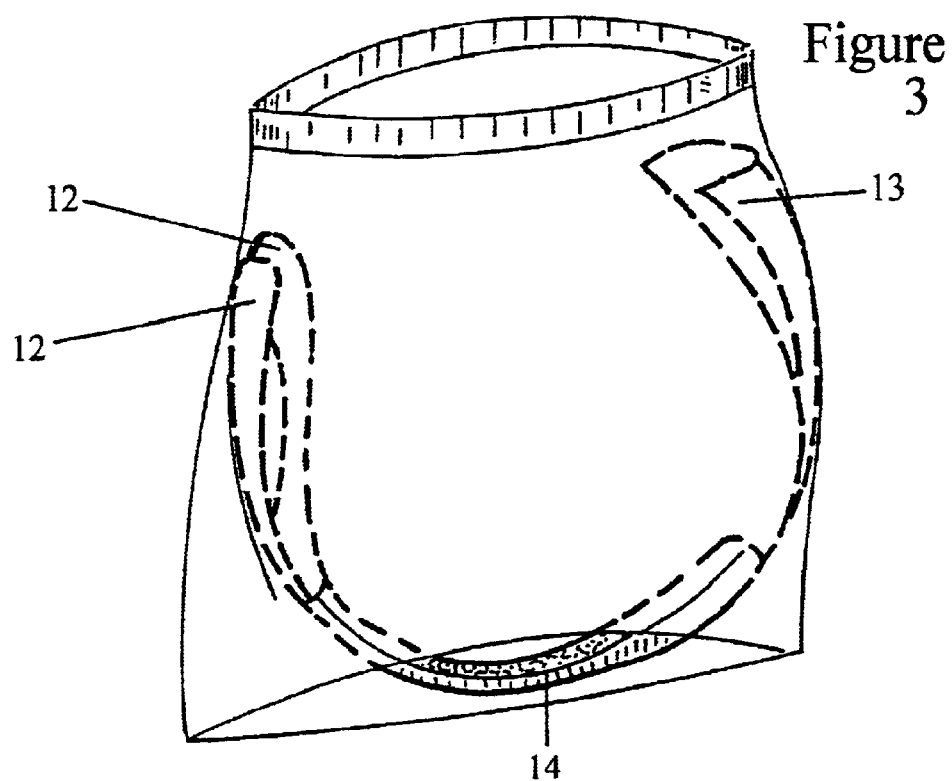
FIG. 3 is a schematic perspective side view of the protective element of FIG. 1 when it is applied to a patient.
Figure 4:
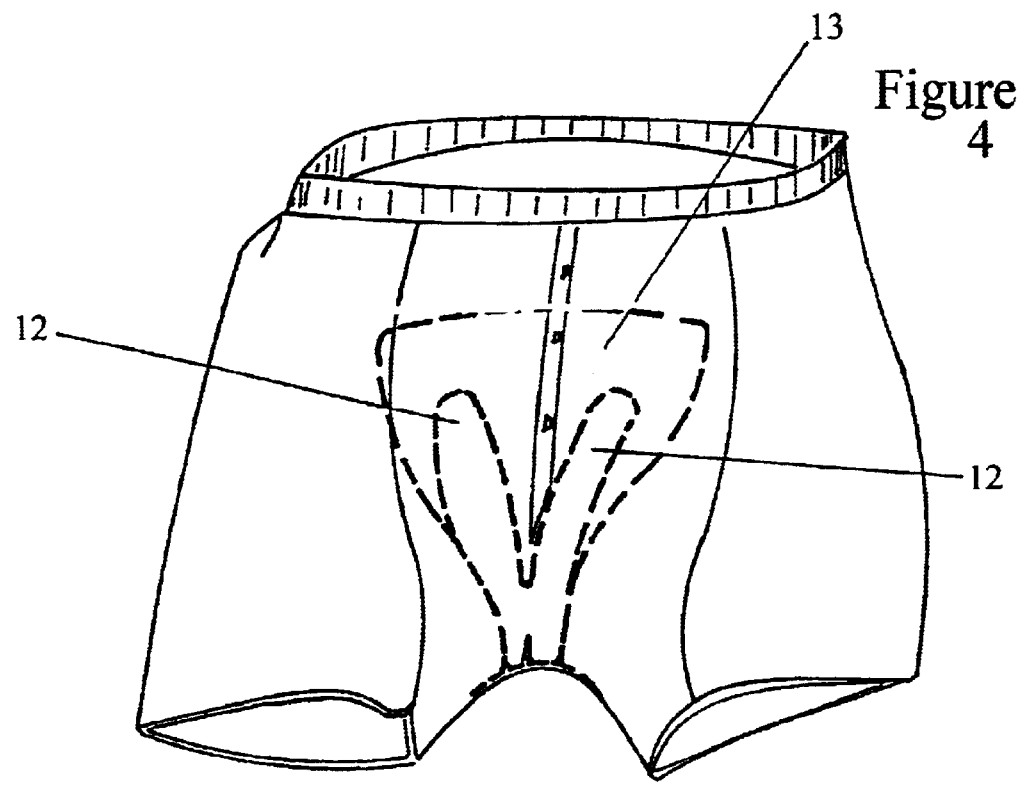
FIG. 4 is a front view of the element of FIG. 1 applied to the patient as shown in FIG. 3.
Figure 5:
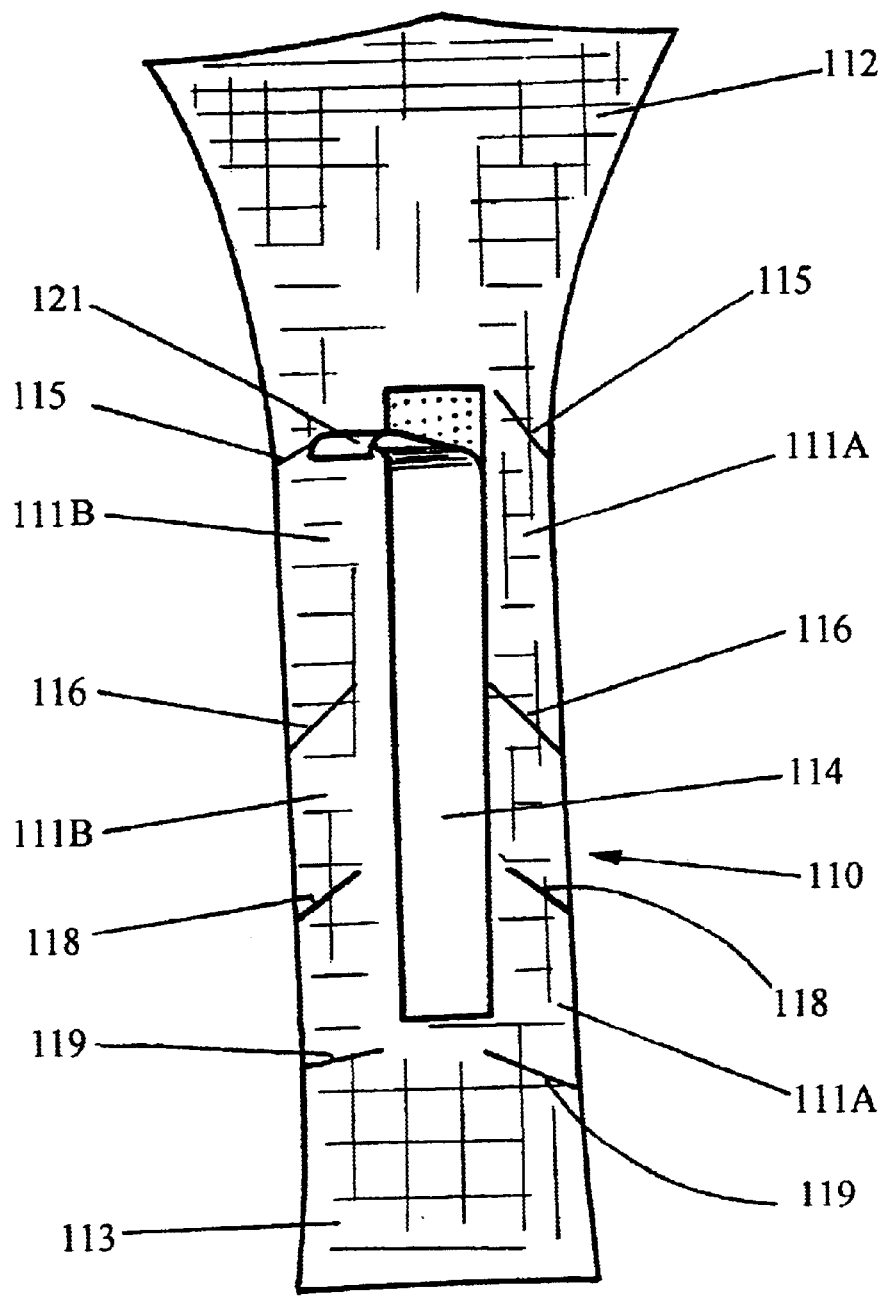
FIG. 5 is a plan view of a protective element according to a second embodiment of the present invention which is designed for a female patient.
Figure 6:
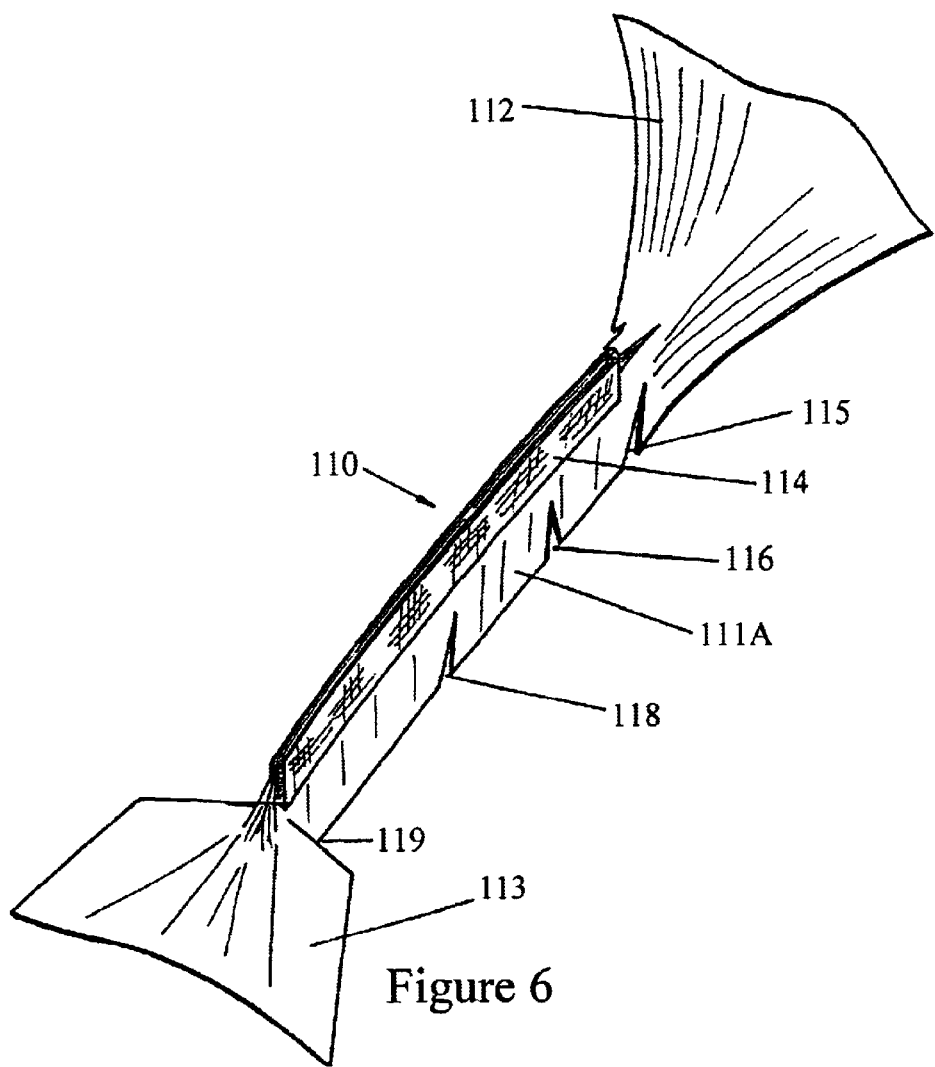
FIG. 6 is a perspective view of the protective element of FIG. 5.
Figure 7:
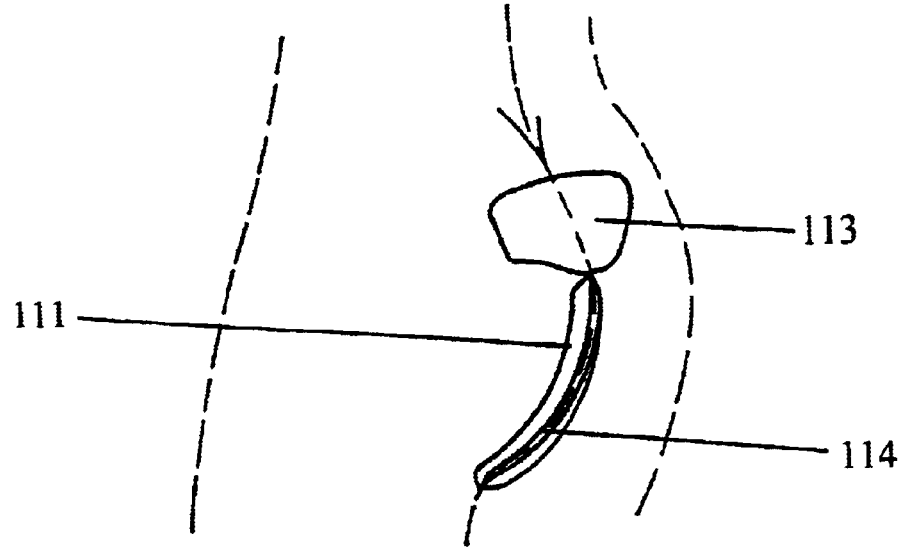
FIG. 7 is a schematic perspective side view of the protective element of FIG. 5 when it is applied to a patient.
Figure 8:
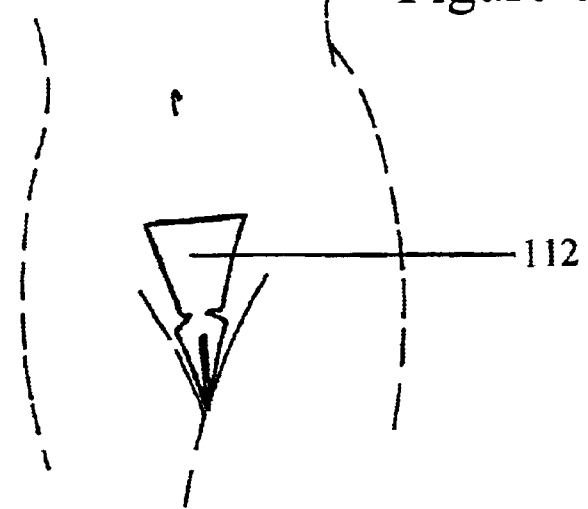
FIG. 8 is a front view of the element of FIG. 5 applied to the patient as shown in FIG. 7.

Furthermore, between the extremities formed by flaps 12 and section 13 and in the lateral wings 11A and 11B of the central part 11, various symmetrical cuts 15, 16, 18, 19 are applied which are meant to allow the protective element 10 to conform to the curved contour of the patient as highlighted in FIGS. 3 and 4. As described below, the protective element 10 will bend over itself such that the spongy strip 14 will form a central U-shaped cushion and the symmetrical cuts 15, 16, 18 and 19 will allow the lateral wings 11A and 11B to diverge from the U-shaped cushion conforming to the shape of the patient.

Figure 2:
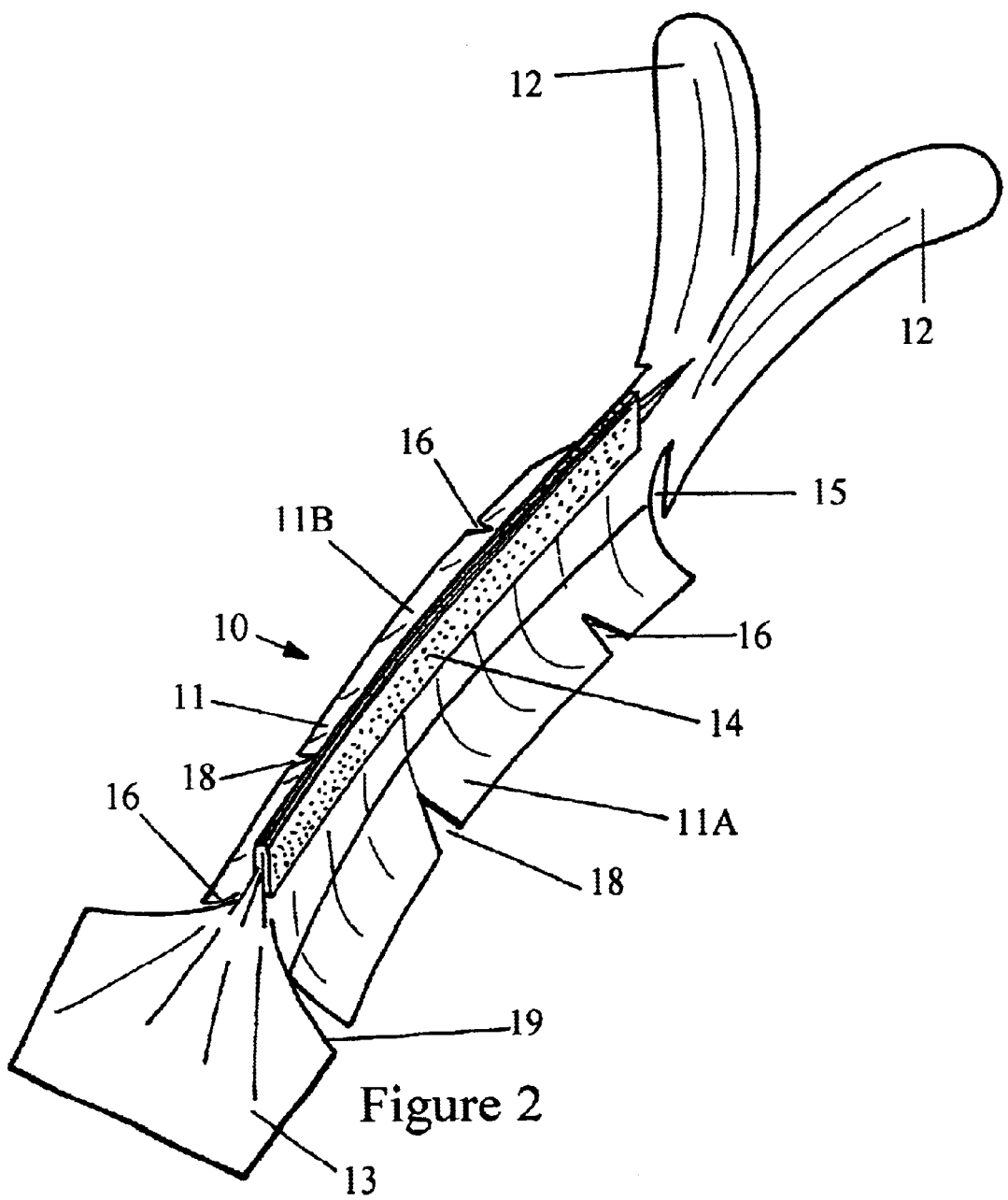
FIG. 2 is a perspective view of the protective element of FIG. 1.
Figure 9:
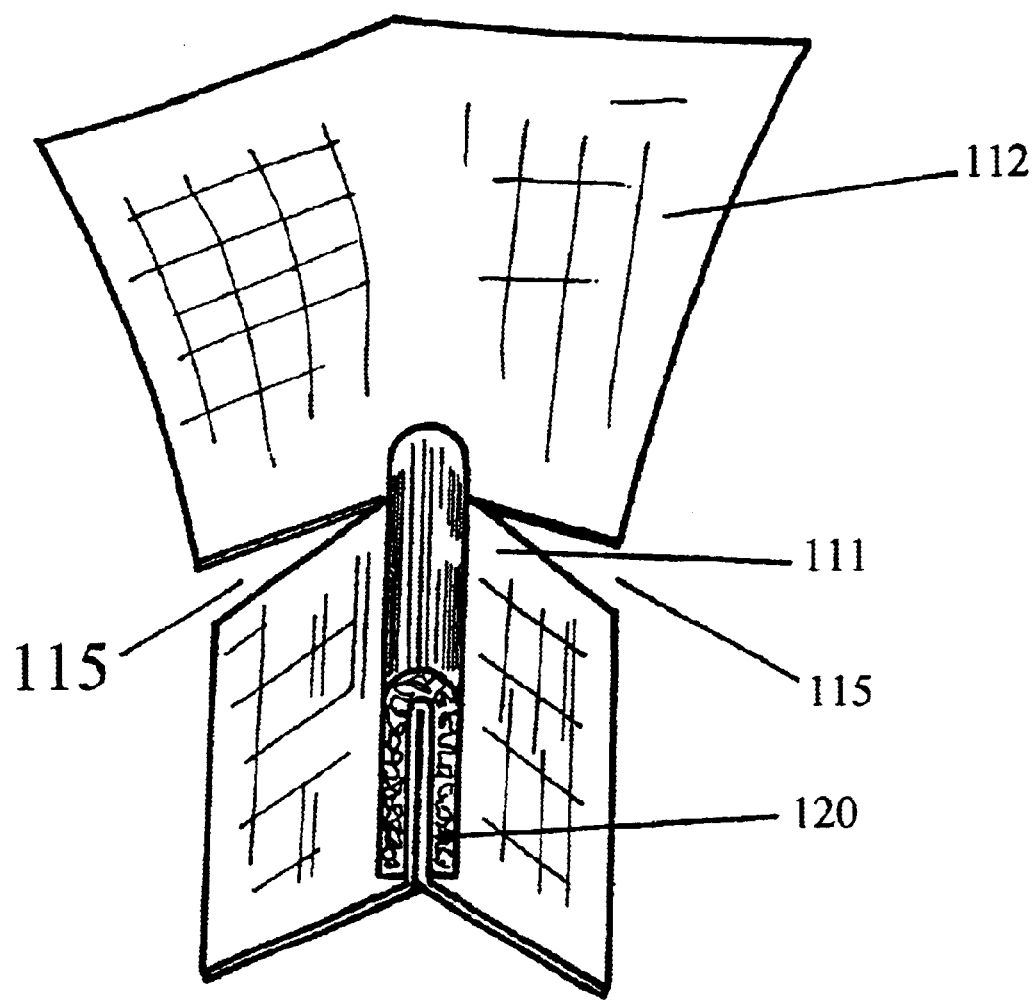
FIG. 9 is a transverse sectional view of the protective element of FIGS. 5–8 in a position to be inserted in place in the patient.

With the element 10 structured as described above, the element 10 may be folded along a longitudinal center line so that the spongy rectangular strip 14 will bend in the transverse section (as shown in FIG. 2) into a thin U-shaped configuration. Essentially, the central part 11 to which the strip 10 is attached is folded to contact itself as shown in FIG. 9. This configuration allows the protective element 10 to fit correctly to the patient's anatomy to fulfill its intended function. The protective wings 11A, 11B prevent lateral secretion.

Regarding the anterior part formed by flaps 12 of the protective element 10 (FIGS. 1–4), it is important to highlight that the particular V-shaped configuration is adapted to the male anatomy.

The protective element 110 shown in FIGS. 5–8 is substantially similar to the protective element 10 shown in FIGS. 1–4. One can observe that the structure of protective element 110 is designed for a female patient. It is practically identical to element 10. The differences lie in the form of the anterior part 112 which is substantially in a trapezoid shape.

In the body 111 of the element 110, between the anterior and posterior parts 112 and 113, are pairs of symmetrical cuts 115, 116, 118, 119, that allow curvature for the element 110 to fold onto itself to form a very tight U shape, with the rectangular central strip 114. Formed laterally of the body 111 and the center strip 114, are wings 111A and 111B which are necessary to prevent the loss of secretions, exudations or the like or of a topical substance placed on the central strip laterally of the element 110.

Regarding the material to be used for the protective element 10 or 110, preferably it will be a tissue (not a woven fabric) for both the main body and the cushion or strip 14. These may be formed of 70% polyester fiber and 30% non-resin fibers. It is important to point out that the union of fibers is obtained by water jets at high pressure, while the absence of any resinating procedures make the material completely non-allergenic, soft and elastic, all characteristics which are necessary to have it conform to the anatomy of a patient whether male or female, and in order to adapt it to the patient's anatomy allowing for movement to prevent epidermal abrasions.

As already mentioned, the central strip 14, can be impregnated with any topical substance which can be released to the patient such as a pharmacological substance, for example, anaesthetics, softeners, antibiotics, disinfectant substances, etc. In cases in which the central strip 14 is impregnated with one of the above substances, it is preferable to have it covered with an impermeable cover 21, 121, respectively, that can be removed at the time of use in order to avoid dispersion or dryness of the substance.

It will be apparent to those of ordinary skill in the art that various modifications may be made to the present invention without departing from the spirit and scope thereof. The scope of the present invention is defined by the appended claims and equivalence thereto.

I claim:

1. A soft protective flexible element for a female patient for a perineal inguinal area that can absorb any liquid comprising:
   - a strip shaped main body with two lateral protective wings;
   - a central rectangular strip applied to the main body, the central strip is a spongy absorbent cushion; and
   - a posterior and an anterior portion attached to opposed ends of the main body with each portion having a width greater than the width of the main body, wherein the anterior portion of the element for the female patient is a trapezoid shape.

2. The element of claim 1, wherein the lateral wings of the main body include a plurality of transverse cuts that permit the element to conform to the area of the patient to which it is applied, and permits the central strip to be folded onto itself as a U shape in cross-section.

3. The element of claim 1, wherein the rectangular strip is folded in a U shape at application to the patient and is impregnated with substances which can be released gradually to the patient.

4. The element of claim 3, wherein the rectangular strip impregnated with substances to be released is covered with an impermeable cover that is removed at application in order to protect the impregnated strip.

5. A flexible protective element for the perineal area of a patient comprising:
   - a strip shaped flexible main body having a central portion and a pair of lateral wings, the main body defining a longitudinal axis; and
   - a rectangular absorbent cushion attached to the central portion of the main body along the longitudinal axis, wherein the flexible main body and the cushion are adapted to be folded about the longitudinal axis such that the cushion and the central portion of the main body form a U shape in cross-section with the central portion of the main body folded to contact itself and the lateral wings diverging from the U shape to conform to the patient,
   - wherein the protective element further includes a plurality of transverse cuts in the lateral wings and the transverse cuts permitting the lateral wings to conform to the curved shape of the patient.

6. The protective element of claim 5 further including a posterior portion attached to one end of the main body, the posterior portion having a substantially trapezoidal shape with a width greater than the width of the main body.

7. The protective element of claim 6 further including an anterior portion attached to one end of the main body opposite from the posterior portion, the anterior portion having a width greater than the width of the main body.

8. The protective element of claim 7 wherein the anterior portion is a substantially trapezoidal shape.

9. The protective element of claim 7 wherein the anterior portion includes two diverging flaps forming a V shaped area wherein the anterior portion is adapted to accommodate the male anatomy.

10. The protective element of claim 7 further including a substance impregnating the cushion.

11. The protective element of claim 10 wherein the substance is selected from the group consisting of disinfectants, antibiotics, anesthetics, softeners, and combinations thereof.

12. The protective element of claim 10 further including an impereable removable cover connected to the cushion prior to application to the patient.

13. The protective element of claim 7 wherein the cushion is made from about 70% polyester fiber.

14. A method of applying a protective element to the perineal area of a patient comprising the steps of:
   - providing a protective element formed of a strip shaped flexible main body having a central portion, a pair lateral wings, and a rectangular absorbent cushion attached to the central portion of the main body;
   - folding the element along a longitudinal axis thereof, wherein the flexible main body and the cushion are folded about the longitudinal axis such that the cushion and the central portion of the main body form a U shape in cross-section with the central portion of the main body folded to contact itself and the lateral wings diverging from the U shape to conform to the patient;
   - applying the folded element to the perineal area of the patient.

15. The method of claim 14 wherein the element includes an anterior portion with two diverging flaps forming a V-shaped area wherein applying the element to the patient includes the step of accommodating the male anatomy with the diverging flaps of the anterior portion.

16. The method of claim 14 further including the step of impregnating the cushion with a releasable substance prior to application to the patient wherein the substance is gradually releasable to the patient.

17. The method of claim 16 further including the step of removing a releasable cover from the cushion prior to application of the element to the patient.

\* \* \* \* \*